(12) United States Patent
Reeder et al.

(10) Patent No.: US 8,415,108 B2
(45) Date of Patent: Apr. 9, 2013

(54) METHODS FOR DIAGNOSING INTERSTITIAL CYSTITIS VIA NUCLEAR LOCALIZATION OF BETA-CATENIN

(75) Inventors: Jay E. Reeder, Syracuse, NY (US); Robert D. Mayer, Rochester, NY (US); Mary O'Connell, Penfield, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/741,265

(22) PCT Filed: Nov. 5, 2008

(86) PCT No.: PCT/US2008/082520
§ 371 (c)(1),
(2), (4) Date: Jul. 6, 2010

(87) PCT Pub. No.: WO2009/061847
PCT Pub. Date: May 14, 2009

(65) Prior Publication Data
US 2010/0292170 A1    Nov. 18, 2010

Related U.S. Application Data

(60) Provisional application No. 60/985,476, filed on Nov. 5, 2007.

(51) Int. Cl.
*G01N 33/53*     (2006.01)
*G01N 33/68*     (2006.01)

(52) U.S. Cl. ........................................ 435/7.1; 435/7.21
(58) Field of Classification Search ........................ None
See application file for complete search history.

(56) References Cited

U.S. PATENT DOCUMENTS 5,824,493 A     10/1998  Elgavish
2005/0192262 A1  9/2005  Hagstrom et al.

OTHER PUBLICATIONS

Aust et al. "Altered Distribution of beta-Catenin, and Its Binding Proteins E-Cadherin and APC, in Ulcerative Colitis-Related Colorectal Centers," Modern Pathology 14(1):29-39 (2001).
PCT International Search Report and Written Opinion for PCT/US2008/082520, dated Apr. 22, 2009.

*Primary Examiner* — Christine J Saoud
*Assistant Examiner* — Jon M Lockard
(74) *Attorney, Agent, or Firm* — LeClairRyan, a Professional Corporation

(57) ABSTRACT

Methods for diagnosing a pelvic pain disorder that include analyzing samples for increased levels and/or nuclear accumulation of beta-catenin, which indicates presence of the pelvic pain disorder, particularly interstitial cystitis. Therapeutic treatment of a pelvic pain disorder, particularly interstitial cystitis, includes the administration to a patient of an effective amount of an inhibitor of beta-catenin activity. This can be carried out by direct administration of the therapeutic agent or via gene therapy.

7 Claims, 6 Drawing Sheets

```
mewgyllevtsllaalallqrssgaaaasakelscqeitvplckgigyny    50
tympnqfnhdtqdeaglevhqfwplveiqcspdlkfflcsmytpicledy   100
kkplppcrsvcerakagcaplmrqygfawpdrmrcdrlpeqgnpdtlcmd   150
ynrtdlttaapspprrlpppppgeqppsqsyhgrppgarpphrggrggg    200
ggdaaappargggggqkarppgggaapcepgcqcrapmvsvsserhplyn   250
rvktggiancalpchnpffsqderaftvfwiglwsvlcfvstfatvstfl   300
idmerfkyperpiiflsacylfvsvgylvrlvaghekvacsggapgagga   350
ggaggaaagagaagagaqgpggrgeyeelgaveqhvryettgpalctvvf   400
llvyffgmassiwwvilsltwflaagmkwgneaiagysqyfhlaawlvps   450
vksiavlalssvdgdpvagicyvgnqsldalrqfvlaplviylfigtmfl   500
lagfvslfrirsvikqqdgptkthkleklmirlglftvlyvvpaavvvac   550
lfyeqhnrprweathncpclrdlgpdqarrpdyavfmlkyfmclvvgits   600
gvwvwsgktleswralctrccwaskgaavgggagataagggggpgggggg   650
gpgggggpgggggslysdvstgltwrsqtassvsypkqmplsqv         694
```

Figure 3

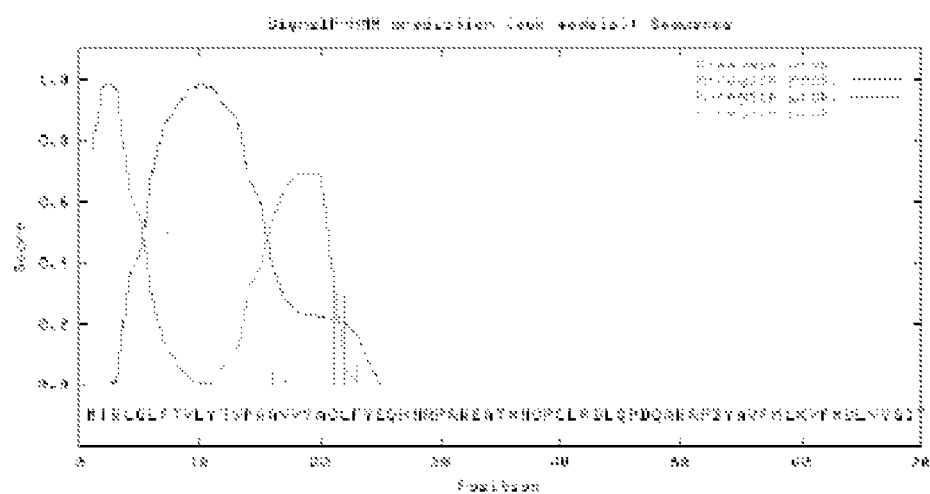

Figure 4

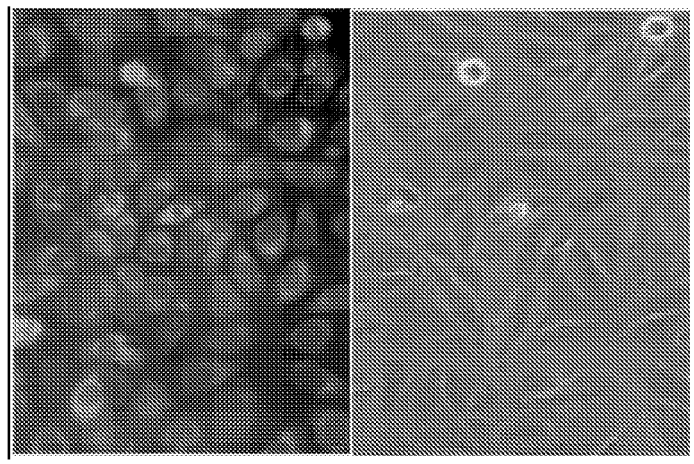

Figure 5A  Figure 5B

```
        V  L  A  F  L  V  I  Y  L  F  I  G  T  N  F  L
     TCGTGCTGGCGCCGCTGGTCATCTACCTCTTCATCGGCACCATGTTCCTG
                                 ||||||||||
     CGCGGATCCAGAACGCTCGGTTCGCTGGCTTTGATTAAAACGTTCCTG

L  A  G  F  V  S  L  F  R  I  R  S  V  I  E  Q  Q
     CTGGCCGGCTTCGTGTCCCTGTTCCGCATCCGCTCGGTCATCAAGCAACA
     ||||||||||||||||||||||||||||||||||||||||||||||||||
     CTGGCCGGCTTCGTGTCCCTCTTCCGCATCCGCTCGTCATCAAGCAACA

D  G  P  T  K  T  H  K  L  E  K  L  M  I  R  L  G
     GGACGGCCCCACCAAGACGCACAAGCTGGAGAAGCTGATGATCCGCCTGG
     ||||||||||||||||||||||||||||||||||||||||||||||||||
     GGACGGCCCCACCAAGACCGACAAGCTGGAGAAGCTGATGATCCGCCTGG

L  F  T  V  L  Y  T  V  P  A  A  V  V  V  A  C
     GCCTGTTCACCGTGCTCTACACCGTGCCGGCCGCGGTGGTGGTCGCCTGC
     |||||||||||||||||||||||||||||||||||||||||||||||||
     GCCTGTTCACCGTGCTCTACACCGTGCCGGCCGCGGTGGTGGTCGCC
```

Figure 6

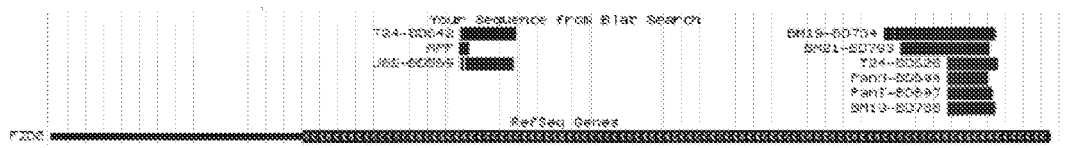

Figure 7

SEQUENCE LISTING

<160> NUMBER OF SEQ ID NOS: 10

<210> SEQ ID NO 1
<211> LENGTH: 694
<212> TYPE: PRT
<213> ORGANISM: Homo sapiens

<400> SEQUENCE: 1

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
        50                  55                  60

Ala Gly Leu Glu Val His Gln Phe Trp Pro Leu Val Glu Ile Gln Cys
65              70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
        130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
            195                 200                 205

Ala Arg Gly Gly Gly Gly Gly Lys Ala Arg Pro Pro Gly Gly Gly
        210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
    290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Ala Gly Gly
            340                 345                 350

```
Ala Gly Gly Ala Ala Ala Gly Ala Gly Ala Gly Ala Gly
        355                 360                 365
Gly Pro Gly Gly Arg Gly Glu Tyr Glu Glu Leu Gly Ala Val Glu Gln
    370                 375                 380
His Val Arg Tyr Glu Thr Thr Gly Pro Ala Leu Cys Thr Val Val Phe
385                 390                 395                 400
Leu Leu Val Tyr Phe Phe Gly Met Ala Ser Ser Ile Trp Trp Val Ile
                405                 410                 415
Leu Ser Leu Thr Trp Phe Leu Ala Ala Gly Met Lys Trp Gly Asn Glu
            420                 425                 430
Ala Ile Ala Gly Tyr Ser Gln Tyr Phe His Leu Ala Ala Trp Leu Val
        435                 440                 445
Pro Ser Val Lys Ser Ile Ala Val Leu Ala Leu Ser Ser Val Asp Gly
    450                 455                 460
Asp Pro Val Ala Gly Ile Cys Tyr Val Gly Asn Gln Ser Leu Asp Asn
465                 470                 475                 480
Leu Arg Gly Phe Val Leu Ala Pro Leu Val Ile Tyr Leu Phe Ile Gly
                485                 490                 495
Thr Met Phe Leu Leu Ala Gly Phe Val Ser Leu Phe Arg Ile Arg Ser
            500                 505                 510
Val Ile Lys Gln Gln Asp Gly Pro Thr Lys Thr His Lys Leu Glu Lys
        515                 520                 525
Leu Met Ile Arg Leu Gly Leu Phe Thr Val Leu Tyr Thr Val Pro Ala
    530                 535                 540
Ala Val Val Val Ala Cys Leu Phe Tyr Glu Gln His Asn Arg Pro Arg
545                 550                 555                 560
Trp Glu Ala Thr His Asn Cys Pro Cys Leu Arg Asp Leu Gln Pro Asp
                565                 570                 575
Gln Ala Arg Arg Pro Asp Tyr Ala Val Phe Met Leu Lys Tyr Phe Met
            580                 585                 590
Cys Leu Val Val Gly Ile Thr Ser Gly Val Trp Val Trp Ser Gly Lys
        595                 600                 605
Thr Leu Glu Ser Trp Arg Ser Leu Cys Thr Arg Cys Cys Trp Ala Ser
    610                 615                 620
Lys Gly Ala Ala Val Gly Gly Ala Gly Ala Thr Ala Ala Gly Gly
625                 630                 635                 640
Gly Gly Gly Pro Gly Gly Gly Gly Gly Pro Gly Gly Gly
                645                 650                 655
Gly Pro Gly Gly Gly Gly Ser Leu Tyr Ser Asp Val Ser Thr Gly
            660                 665                 670
Leu Thr Trp Arg Ser Gly Thr Ala Ser Ser Val Ser Tyr Pro Lys Gln
        675                 680                 685
Met Pro Leu Ser Gln Val
    690

<210> SEQ ID NO 2
<211> LENGTH: 9
<212> TYPE: PRT
<213> ORGANISM: Artificial
<220> FEATURE:
<223> OTHER INFORMATION: Homo sapiens FZD8 peptide, designated
      antiproliferative factor (APF)

<400> SEQUENCE: 2

Thr Val Pro Ala Ala Val Val Val Ala
1               5
```

-continued

```
<210> SEQ ID NO 3
<211> LENGTH: 200
<212> TYPE: DNA
<213> ORGANISM: Homo sapiens

<400> SEQUENCE: 3
tcgtgctggc gccgctggtc atctacctct tcatcggcac catgttcctg ctggccggct      60
tcgtgtccct cttccgcatc cgctcggtca tcaagcaaca ggacggcccc accaagacgc     120
acaagctgga gaagctgatg atccgcctgg gcctgttcac cgtgctctac accgtgcccg     180
ccgcggtggt ggtcgcctgc                                                  200

<210> SEQ ID NO 4
<211> LENGTH: 195
<212> TYPE: DNA
<213> ORGANISM: Artificial
<220> FEATURE:
<223> OTHER INFORMATION: RLM-RACE product

<400> SEQUENCE: 4
cgcggatcca gaacgctgcg tttgctggct tgatgaaaa tgttcctgct ggccggcttc       60
gtgtccctct tccgcatccg ctcggtcatc aagcaacagg acgccccac caagacgcac     120 aagctggaga gctgatgat ccgcctgggc ctgttcaccg tgctctacac cgtgcccgcc     180
gcggtggtgg tcgcc                                                       195

<210> SEQ ID NO 5
<211> LENGTH: 5
<212> TYPE: PRT
<213> ORGANISM: Artificial
<220> FEATURE:
<223> OTHER INFORMATION: Consensus of beta-catenin inhibiting peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Leu Xaa Xaa Leu Leu
1               5

<210> SEQ ID NO 6
<211> LENGTH: 30
<212> TYPE: DNA
<213> ORGANISM: Artificial
<220> FEATURE:
<223> OTHER INFORMATION: sense primer

<400> SEQUENCE: 6
atgatccgcc tgggcctgtt caccgtgctc                                       30

<210> SEQ ID NO 7
<211> LENGTH: 25
<212> TYPE: DNA
<213> ORGANISM: Artificial
<220> FEATURE:
<223> OTHER INFORMATION: antisense primer

<400> SEQUENCE: 7
ctggcccagc agcagcgggt gcaca                                            25

<210> SEQ ID NO 8
<211> LENGTH: 8
<212> TYPE: PRT
<213> ORGANISM: Artificial
```

```
-continued

<220> FEATURE:
<223> OTHER INFORMATION: Homo sapiens FZD8 peptide fragment

<400> SEQUENCE: 8

Tyr Gly Phe Ala Trp Pro Asp Arg
1               5

<210> SEQ ID NO 9
<211> LENGTH: 10
<212> TYPE: PRT
<213> ORGANISM: Artificial
<220> FEATURE:
<223> OTHER INFORMATION: Homo sapiens FZD8 peptide fragment

<400> SEQUENCE: 9

Tyr Glu Thr Thr Gly Pro Ala Leu Cys Thr
1               5                   10

<210> SEQ ID NO 10
<211> LENGTH: 15
<212> TYPE: PRT
<213> ORGANISM: Artificial
<220> FEATURE:
<223> OTHER INFORMATION: Homo sapiens FZD8 peptide fragment

<400> SEQUENCE: 10

Gly Ala Gly Ala Ala Gly Ala Gly Ala Gly Gly Pro Gly Gly Arg
1               5                   10                  15
```

METHODS FOR DIAGNOSING INTERSTITIAL CYSTITIS VIA NUCLEAR LOCALIZATION OF BETA-CATENIN

This application is a national stage application under 35 U.S.C. 371 of PCT/US2008/082520, filed Nov. 5, 2008, and claims the priority benefit of U.S. Provisional Patent Application Ser. No. 60/985,476, filed Nov. 5, 2007, which is hereby incorporated by reference in its entirety.

This invention was made with government support under grant number U01 DK066255-0451 awarded by National Institutes of Health (NIDDK). The government has certain rights in this invention.

FIELD OF THE INVENTION

The present invention relates to the diagnosis and treatment of pelvic pain disorder through detection and inhibition of beta-catenin.

BACKGROUND OF THE INVENTION

Interstitial cystitis ("IC") is an idiopathic illness of visceral hypersensitivity characterized by increased urinary frequency/urgency and pelvic pain for which effective therapy, especially for those with long standing or severe symptoms, remains elusive. The variability in the presentation and comorbid illnesses, whether the primary symptom is pain or urinary frequency, as well as diversity of response to therapies, suggest that IC be viewed as a symptom complex resulting from a variety of separate underlying but potentially interrelated mechanisms rather than a disease with a uniform pathophysiology. There continues to be controversy as to whether the problem is a specific bladder process or a manifestation of a more systemic autoimmune/endocrine disease with regional pelvic visceral/somatic dysfunction.

The absence of an established uniform underlying (and measurable) pathophysiology results in difficulty defining IC and appropriate diagnostic criteria. IC was originally characterized by urinary symptoms and cystoscopic visualization of ulcerations of bladder mucosa. The number of patients diagnosed subsequently was broadened by inclusion of findings of submucosal petechial hemorrhages (glomerulations) following hydrodistension of the bladder under anesthesia. The International Continence Society has proposed the term Painful Bladder Syndrome for patients experiencing a similar symptom complex. It has been reported, however, that a number of IC patients may be excluded under this new definition (Warren et al., "Using the International Continence Society's definition of painful bladder syndrome," *Urology* 67:1138-1142 (2006)). A test has been promoted for diagnosis utilizing intravesical instillation of concentrated potassium chloride and recording whether this elicits bladder discomfort (Parsons et al., "Prevalence of interstitial cystitis in young women," *Urology* 64:866-870 (2004)). Both cystoscopy and the potassium sensitivity test are reported to have shortcomings in regard to sensitivity and specificity. The literature regarding hydrodistension is complicated by the lack of a consensus in protocol/methodology in performing the procedure, with a study revealing a wide variability in the practice (Turner et al., "How do you stretch a bladder? A survey of UK practice, a literature review, and a recommendation of a standard approach," *Neurourol Urodyn* 24:74-76 (2005)). It has also been recently reported that the appearance of glomerulations is not constant and may develop over time (Shear et al., "Development of glomerulations in younger women with interstitial cystitis," *Urology* 68:253-256 (2006)).

The spectrum of severity of symptoms and the difficulties encountered with hydrodistension and potassium sensitivity testing are such that biomarkers have been evaluated as an aid to diagnosis. The most comprehensive report compared a number of putative biomarkers in an IC population. While antiproliferative factor ("APF") appeared to be the most specific for IC (Erickson et al., "A comparison of multiple urine markers for interstitial cystitis," *J Urol* 167:2461-2469 (2002)), a reliable commercial assay for APF has yet to be developed and the control of its production and its role in actually causing symptoms remains uncertain. Although there is a trend to make a diagnosis based on symptoms and an office test such as intravesical potassium sensitivity, IC still remains a diagnosis of exclusion, and reasonable attempts should be made to find a correctable underlying etiology.

The etiology of IC is still uncertain and may consist of multiple coexisting and reinforcing mechanisms. Prevalent theories include possible infectious origin, bladder permeability defects, local neurogenic and histamine-induced inflammation, as well as a more generalized vulnerability to visceral hypersensitivity due to genetic or acquired abnormalities of the immune or neuroendocrine system.

Recent advances have demonstrated that the urothelium and its innervations are much more complex than previously thought, with a variety of interrelated pathways that may in part explain IC pathogenesis (Kanai et al., "Symposium report on urothelial dysfunction: pathophysiology and novel therapies" *J. Urol.* 175:1624-1629 (2006); Steers et al., "Mechanisms of disease: the role of nerve growth factor in the pathophysiology of bladder disorders," *Nat Clin Pract Urol* 3:101-110 (2006)). IC bladders demonstrate abnormal secretion of APF, nerve growth factor, inflammatory cytokines, ATP and multiple other signaling molecules. Abnormal production of some of these substances can persist once cells are removed from the urinary environment and grown in culture (Ruggieri, "Mechanisms of disease: role of purinergic signaling in the pathophysiology of bladder dysfunction" *Nat Clin Pract Urol* 3:206-215 (2006); Sun et al., "Augmented extracellular ATP signaling in bladder urothelial cells from patients with interstitial cystitis" *Am J Physiol Cell Physiol* 290:C27-C34 (2006)). These abnormalities in cellular signaling have yet to be fully explored in regard to opportunities for diagnosis or treatment.

There is also increasing awareness in those treating IC that the pathology and abnormal physiology associated with IC may well extend outside the bladder, requiring a broader view of therapeutic targets. IC is a syndrome defined by bladder symptoms, but it has been appreciated that IC patients will often have an increased prevalence of certain comorbid illnesses including allergies, irritable bowel syndrome, and fibromyalgia. When compared with the general population, the incidence of inflammatory bowel disease was estimated to be about 30 times more common in IC patients who had ulcers than in the general population (Peeker et al., "Intercurrent autoimmune conditions in classic and nonulcer interstitial cystitis," *Scand J Urol Nephrol* 37:60-63 (2003)). A study (Warren et al., "Prevalence of interstitial cystitis in first-degree relatives of patients with interstitial cystitis," *Urology* 63:17-21 (2004)) evaluating possible genetic influences found a 17-fold greater prevalence of the disease in adult first degree relatives of women with IC, suggesting a genetic predisposition to a hypersensitivity syndrome. The effects of hormonal cycle have been documented in IC patients and reveal alterations of pain sensitivity and bladder functioning during the menstrual cycle. This suggests, therefore, the possibility of hormonal manipulation in patients so affected, but this has not been rigorously tested (Powell-Boone et al., "Menstrual cycle affects bladder pain sensation in subjects with interstitial cystitis," *J Urol* 174:1832-1836 (2005)). Advances in the future treatment of IC will likely depend on finding methods to better identify subgroups of patients with improved likelihood of response to certain types of therapy.

The present invention is directed to overcoming these and other deficiencies in the art.

SUMMARY OF THE INVENTION

A first aspect of the present invention relates to a method for diagnosing a pelvic pain disorder that includes: obtaining a sample from a subject; and analyzing said sample for increased levels or sub-cellular localization of beta-catenin, which indicates presence of the pelvic pain disorder. This aspect of the present invention is particularly effective in diagnosing interstitial cystitis, preferably when used in combination with an assessment of presented patient symptoms.

A second aspect of the present invention relates to a method of treating a pelvic pain disorder in a patient that includes administering to the patient experiencing pelvic pain, or having previously experienced pelvic pain, an effective amount of an inhibitor of beta-catenin activity. According to this aspect of the invention, treatment of the pelvic pain disorder can be effective to mitigate symptoms of the pelvic pain disorder, particularly for interstitial cystitis.

A third aspect of the present invention relates to a method of characterizing response to treatment for a pelvic pain disorder that includes the steps of measuring a level of and/or localization of beta-catenin in a sample obtained from a patient to be treated for a pelvic pain disorder; treating the patient with an inhibitor of beta-catenin; and repeating said measuring after said treating, whereby a decrease in the beta-catenin level or a decrease in nuclear localization following said treating indicates that the treatment is effective.

BRIEF DESCRIPTION OF THE DRAWINGS

FIG. 3 shows the amino acid sequence of FZD8 (SEQ ID NO: 1). The seven transmembrane domains predicted by computer algorithm (Cserzo et al., "Prediction of Transmembrane alpha-helices in procariotic membrane proteins: the Dense Alignment Surface method," *Prot Eng.* 10(6):673-676 (1997), which is hereby incorporated by reference in its entirety) are highlighted. The APF sequence, TVPAAVVVA (SEQ ID NO: 2), is shown in capital letters.

FIG. 4 shows initiation of FZD8 translation at the most proximal 5' methionine codon relative to the APF peptide is predicted to produce a signal peptide for ER/golgi processing of the protein and appropriate amino terminal cleavage of the APF sequence. The APF peptide sequence, TVPAAVVVA, spans from position 12 to 20 of the polypeptide sequence shown (fragment of SEQ ID NO: 1). It is believed that the cleaved peptide could be subsequently processed to produce the secreted APF peptide, and that the seventh transmembrane domain and intracellular carboxy terminus disrupts normal urothelial function in IC. The putative APF precursor protein sequence was analyzed using SignalP. The graph shows the output of the Hidden Markov Model analysis (Bendtsen et al., "Improved prediction of signal peptides: SignalP 3.0," *J Mol Biol.* 340(4):783-95 (2004), which is hereby incorporated by reference in its entirety).

FIG. 5A-B show the expression of putative APF precursor protein fused to green fluorescent protein in J82 cells. FIG. 5A shows the cytoplasmic, granular fluorescence is consistent with the distribution of a protein in the secretory pathway. FIG. 5B shows the corresponding phase image of the same live cells.

FIG. 6 shows FZD8 RLM-RACE product from J82 urothelial cells. A portion of the FZD8 open reading frame (SEQ ID NO: 3) and the corresponding amino acid sequence (fragment of SEQ ID NO: 1) are shown in alignment with the PCR product from RLM-RACE (SEQ ID NO: 4). The RACE product was sequenced with a primer sequence in the 5' adaptor (underlined) and a primer complementary to the APF coding sequence. Translation of an mRNA transcript with this 5' end would be expected to begin at the double underlined methionine codon, which represents the internal translation site identified by the Hidden Markov Model (see FIG. 4).

FIG. 7 shows RLM-RACE results. BM19 and BM21 are IC biopsies; Normal and tumor samples from pancreas are labeled PanN and PanT; and J82 and T24 are bladder cancer cell lines.

FIG. 11A is from a control patient, FIG. 11C is from an IC patient, and FIG. 11B shows the overlay in which several differentially expressed proteins can be seen.

DETAILED DESCRIPTION OF THE INVENTION

Figures 1A, 1B:
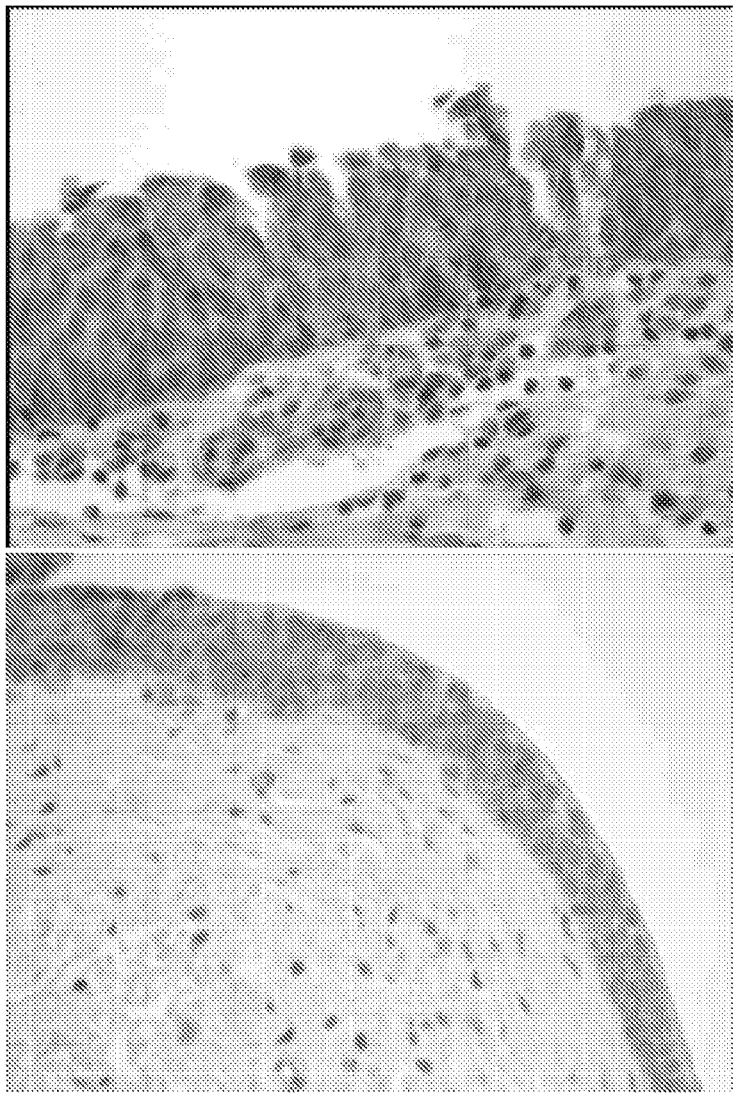
FIGS. 1A-B show immunohistochemistry for FZD8 protein expression in normal urothelium from a bladder cancer patient (FIG. 1A) and in a bladder biopsy from an IC patient (FIG. 1B).

The present invention relates generally to the diagnosis and treatment of pelvic pain disorders, including bladder disorders that are characterized by increased expression and/or reduction in degradation of beta-catenin. Exemplary pelvic pain disorders include, without limitation, pain disorders involving the bladder (e.g., interstitial cystitis), pain disorders involving the bowel (e.g., Crohn's disease, ulcerative colitis, irritable bowel syndrome, etc.), as well as pain disorders involving the reproductive organs or tissues such as the uterus, vagina, cervix, testis, prostate, and epididymis (e.g., vulvodynia, vestibulitis, endometriosis, prostatitis, orchalgia, proctalgia). With respect to such diagnosis and treatment, samples will be taken from and therapeutics administered to individuals (e.g., patients).

As used herein, "patient" or "individual" refers to any mammal that exhibits a pelvic pain disorder. Preferably, the patient or individual is one having a pelvic pain disorder such as interstitial cystitis, which is characterized by increased expression of and/or reduction in degradation of beta-catenin. Exemplary mammals include, without limitation, humans and other primates, cats, dogs, cows, horses, pigs, sheep, and rodents such as mice and rats. According to one embodiment, the patient is a female.

Suitable sample materials from the patient are preferably fluid samples, including, without limitation, blood, urine, and spinal fluid. Of these, urine is preferred. Alternatively, solid tissue samples can also be used. These include, without limitation, fine needle aspiration, core needle biopsies, a surgical biopsies, vacuum-assisted biopsies, biopsies using an advanced breast biopsy instrument, surgical specimen, paraffin embedded tissue, and frozen tissue imprints. The use of other types of samples is also contemplated.

In certain embodiments, whole tissue samples can be analyzed, whole cells can be analyzed, cell fractions (e.g., nuclear or cytoplasmic fractions) can be analyzed, or extracellular fluids can be analyzed for beta-catenin. The presence of a pelvic pain disorder can be assessed by the detection of increased levels or sub-cellular localization of beta-catenin, preferably in combination with other symptoms associated with the particular pelvic pain disorder. In one embodiment, increased nuclear localization of beta-catenin is associated with interstitial cystitis.

Measuring beta-catenin levels in a patient sample (or sub-cellular localization within cells from a patient sample) can be performed with a suitable assay system.

According to one approach, the assay system utilizes an immunological detection procedure, using an antibody or binding portion thereof that specifically recognizes or binds to beta-catenin. Exemplary anti-beta-catenin antibodies include, without limitation, polyclonal antibodies (available from Abcam, Santa Cruz, Sigma, Invitrogen, etc.) and monoclonal antibodies (available from Santa Cruz, Sigma, Transduction Laboratories, Invitrogen, etc.). One preferred antibody is a mouse monoclonal anti-beta-catenin antibody available from Invitrogen/Zymed (catalog #18-0226).

The patient sample is contacted with the antibody or binding portion thereof and any reaction which indicates that beta-catenin is present in the patient sample is detected. Detection of antibody/beta-catenin binding can be achieved using any of a variety of known detection procedures, such as enzyme-linked immunoabsorbent assay, radioimmunoassay, gel diffusion precipitin reaction assay, immunodiffusion assay, agglutination assay, fluorescent immunoassay, protein A immunoassay, or immunoelectrophoresis assay.

Alternatively, beta-catenin levels in a patient sample can be measured using HPLC or mass spectrometry. The use of HPLC and mass spectrometry detection procedures are well known in the art.

Finally, beta-catenin levels can be reflected by the amount of beta-catenin mRNA present in cells or in tissue. The level of mRNA corresponding to the beta-catenin gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length beta-catenin nucleic acid, such as the nucleic acid of Genbank Accession No. NM_001098209, NM_001098210, and NM_001904 (each of which is hereby incorporated by reference in its entirety) or a portion thereof, such as an oligonucleotide of at least 7, 15, 30, 50, 100, 250 or 500 nucleotides in length and sufficient to specifically hybridize under stringent conditions to beta-catenin mRNA or genomic DNA. The probe can be disposed on an address of an array. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt other known mRNA detection methods for use in detecting the level of mRNA encoded by the beta-catenin gene.

The level of mRNA in a sample that is encoded by the beta-catenin gene can also be evaluated with nucleic acid amplification, e.g., by RT-PCR (U.S. Pat. No. 4,683,202 to Mullis, which is hereby incorporated by reference in its entirety), ligase chain reaction (Barany, "Genetic Disease Detection and DNA Amplification using Cloned Thermostable Ligase," *Proc. Natl. Acad. Sci. USA* 88(1):189-193 (1991), which is hereby incorporated by reference in its entirety), self sustained sequence replication (Guatelli et al., "Isothermal, in vitro Amplification of Nucleic Acids by a Multienzyme Reaction Modeled after Retroviral Replication," *Proc. Natl. Acad. Sci. USA* 87(5):1874-1878 (1990), which is hereby incorporated by reference in its entirety), transcriptional amplification system (Kwoh et al., "Transcription-based Amplification System and Detection of Amplified Human Immunodeficiency Virus Type 1 with a Bead-based Sandwich Hybridization Format," *Proc. Natl. Acad. Sci. USA* 86(4):1173-1177 (1989), which is hereby incorporated by reference in its entirety), rolling circle replication (U.S. Pat. No. 5,854,033 to Lizardi et al., which is hereby incorporated by reference in its entirety) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes beta-catenin (or a fragment thereof).

The present invention also relates to methods of treating a pelvic pain disorder in a patient that includes administering to the patient experiencing pelvic pain, or having previously experienced pelvic pain, an effective amount of an inhibitor of beta-catenin activity. According to this aspect of the invention, treatment of the pelvic pain disorder can be effective to mitigate symptoms of the pelvic pain disorder, particularly for interstitial cystitis.

Any of one or more different inhibitors of beta-catenin can be used, as well as combinations thereof. These can include, without limitation, small molecule inhibitors, protein and peptide inhibitors, and antisense (RNAi) inhibitors.

Exemplary small molecule inhibitors include, without limitation, quercetin (Park et al., "Quercetin, a potent inhibitor against beta-catenin/Tcf signaling in SW480 colon cancer cells," *Biochem Biophys Res Commun.* 328(1):227-34 (2005), which is hereby incorporated by reference in its entirety; compounds such as ZTM000990, PKF118-310, PKF118-744, PKF115-584, PKF-222-815, CPG049090, PNU-74654, ICG-001, NSC668036, and others disclosed in Trosset et al., "Inhibition of protein-protein interactions: The discovery of druglike beta-catenin inhibitors by combining virtual and biophysical screening," *In Proteins: Structure, Function, and Bioinformatics* 64(1):60-67 (2006) and Barker et al., "Mining the Wnt Pathway for Cancer Therapeutics," Nature Reviews Drug Discovery 5:997-1014 (2006), each of which is hereby incorporated by reference in its entirety; LC-363 (Avalon Pharmaceuticals, Germantown, Md.); compounds such as N'-[(E)-(5-methyl-2-furyl)methylidene]-2-phenoxybenzohydrazide, N'-[(E)-1-(5-methyl-2-thienyl)ethylidene]-2-phenoxyacetohydrazide, 5-[2-(5-methyl-2-furyl)ethyl]-2-(2-thienyl)-1H-indole, 2-(2-furyl)-5-[(E)-2-(5-methyl-2-furyl)ethenyl]-1H-indole, N-[(E)-(5-methyl-2-furyl)methylidene]-4-(4-pyridinyl)-8-quinolin-amine, 2-(2-furyl)-5-[2-(5-methyl-2-furyl)ethyl]-1H-indole, 7-{(2E)-2-[(5-methyl-2-furyl)methylene]hydrazino}-N-(2-phenylethyl)-5,6-dihydrobenzo[h]isoquinoline-9-carboxamide, 1-{[(E)-(5-methyl-2-furyl)methylidene]amino}-3-(4-pyridinyl)-2,4-(1H,3H)-quinazolinedione, N-(5-methyl-2-furyl)-N-(2'-phenoxy[1,1'-biphenyl]-3-yl)amine, 4-{[7-(5-methyl-2-furyl)-2-naphthyl]oxy}pyridine, N-(5-bromo-1,3,4-oxadiazol-2-yl)-4-hydroxy-2-oxo-6-phenyl-2H-pyran-3-carboxamide, 4-hydroxy-N-(5-methyl-2-furyl)-2-oxo-6-phenyl-2H-pyran-3-carbox-amide, 3-[(E)-2-(5-bromo-1,3,4-thiadiazol-2-yl)ethenyl]-4-hydroxy-6-ph-enyl-2H-pyran-2-one, N-(5-bromo-1,3,4thiadiazol-2-yl)-4-hydroxy-2-oxo-6-phenyl-2H-pyran-3-carboxamide, 5-[(3-amino-1H-1,2,4-triazol-5-yl)methyl]-3-[3-fluoro-4-(4-morpholinyl)phenyl]-1,3-oxazolidin-2-one, 4-[(3-amino-1H-1,2,4-triazol-5-yl)methyl]-1-[3-fluoro-4-(4-morpholinyl)phenyl]-2-imidazolidinone, 1-benzhydryl-4-(5-bromo-2-furoyl)piperazine, 1-benzhydryl-4-[(5-methyl-2-thienyl)carbonyl]piperazine, benzyl (2E)-2-[1-(4-methyl-2-thienyl)ethylidene]hydrazinecarboxylate, 2-(4-chlorophenyl)-6-methyl-5-(5-methyl-1,3,4-oxadiazol-2-yl)[1-,3]thiazolo[3,2-b][1,2,4]triazole, N-(5-methyl-3-isoxazolyl)-N'-[(5-phenyl-1,3,4-oxadiazol-2-yl)carbonyl]urea, N-[3-(2-{[(5-chloro-2-thienyl)methyl]sulfonyl}hydrazino)-3-oxopropyl]benzenesulfonamide-5-[3-(4-phenoxyphenyl)propyl]-1,3,4-oxadiazol-2-ol, N-(3-methyl-5-isoxazolyl)-4-phenoxybenzamide, 4-hydroxy-N-(3-methyl-5-isoxazolyl)-2-oxo-6-phenoxy-2H-pyran-3-carboxamide, 2-phenoxy-N'-[(Z)-phenyl(2-thienyl)methylidene]benzo-hydrazide, 2-anilino-N'-[(Z)-2-furyl(phenyl)methylidene]benzohydrazide, 4-[(Z)-1-(3-methyl-5-isoxazolyl)-2-phenylethenyl]phenyl 2-(1-pyrrolidinyl)ethyl ether, 5-methyl-2-furaldehyde [(3Z)-2-oxo-1-(4-pyridinyl)-1,2-dihydro-3H-indol-3-ylidene]hydrazone, (2Z)-N-[(5-methyl-2-furyl)methyl]-2-[2-oxo-1-(4-pyridinyl)-1,2-dihydro-3H-indol-3-ylidene]ethanamide, (2Z)-N-[(3-methyl-5-isoxazolyl)methyl]-2-[2-oxo-1-(4-pyridinyl)-1,2-dihydro-3H-indol-3-ylidene]ethanamide, (2-chloro-1,3-thiazol-5-yl)methyl 4-(4-morpholinylsulfonyl)phenyl ether, N-(4,5-dihydronaphtho[1,2-d][1,3]thiazol-2-yl)-N-(4-phenoxybutyl)methanesulfonamide, N-(6-methoxy-4,5-dihydronaphtho[1,2-d][1,3]thiazol-2-yl)-N-[2-(1-methyl-3-phenylpropoxy)ethyl]acetamide, 4-{2-[(5-methyl-2-furyl)methoxy]benzylidene}-1-(4-pyridinylsulfonyl)piperidine, 4-{2-[(5-bromo-2-furyl)methoxy]benzylidene}-1-isonicotinoylpiperidine, N-(4,5-dihydronaphtho[1,2-d][1,3]thiazol-2-yl)-N-(4-phenylpentyl)acetamide, N-(4,5-dihydro-3H-naphtho[1,2-d]imidazol-2-yl)-N-[2-(2-phenylethoxy)ethyl]methanesulfonamide, N'-[(Z)-(5-methyl-2-furyl)(2-pyridinyl)methylidene]-2-phenoxybenzohydrazide, and their pharmaceutically acceptable salts as disclosed in US Patent Application Publ. No. 20040204477 to Moll et al., which is hereby incorporated by reference in its entirety; hydroxymatairesinol (U.S. Pat. No. 6,271,257 to Mutanen, which is hereby incorporated by reference in its entirety); hexachlorophene (Park et al., "Hexachlorophene Inhibits Wnt/β-Catenin Pathway by Promoting Siah-Mediated β-Catenin Degradation," Molecular Pharmacology *Fast Forward* (May 30, 2006), which is hereby incorporated by reference in its entirety); and PPARγ agonists (e.g., troglitazone) and PPARγ-inactive analogs (e.g., Δ2TG and STG28) (Wei et al., "Thiazolidinediones Modulate the Expression of β-Catenin and Other Cell-Cycle Regulatory Proteins by Targeting the F-Box Proteins of Skp1-Cull-F-box Protein E3 Ubiquitin Ligase Independently of Peroxisome Proliferator-Activated Receptor γ," *Molecular Pharmacology Fast Forward* (Jun. 14, 2007), which is hereby incorporated by reference in its entirety).

Exemplary protein and peptide inhibitors include, without limitation, chibby overexpression (Schuierer et al., "Reduced expression of β-catenin inhibitor Chibby in colon carcinoma cell lines," *World J Gastroenterol* 12(10):1529-1535 (2006), which is hereby incorporated by reference in its entirety); Axin overexpression (Nakamura et al., "Axin, an inhibitor of the Wnt signalling pathway, interacts with beta-catenin, GSK-3beta and APC and reduces the beta-catenin level," *Genes Cells* 3:395-403 (1998), which is hereby incorporated by reference in its entirety); HDPR1 overexpression (Yao et al., "HDPR1, a novel inhibitor of the WNT/beta-catenin signaling, is frequently downregulated in hepatocellular carcinoma: involvement of methylation-mediated gene silencing," Oncogene 24:1607-1614 (2005), which is hereby incorporated by reference in its entirety); ICAT overexpression (Tago et al., "Inhibition of Wnt signaling by ICAT, a novel beta-catenin-interacting protein," *Genes Dev.* 14:1741-1749 (2000); Genbank Accession No. BAB03458, each of which is hereby incorporated by reference in its entirety); and LXXLL (SEQ ID NO: 5) peptides of the type disclosed in U.S. Pat. No. 6,677,116 to Blaschuk et al., which is hereby incorporated by reference in its entirety. These protein or polypeptide inhibitors can be administered directly or expressed in vivo via gene therapy approaches, discussed below.

Exemplary antisense beta-catenin constructs include those reported in Green et al., "Beta-catenin Antisense Treatment Decreases Beta-catenin Expression and Tumor Growth Rate in Colon Carcinoma Xenografts," *J Surg. Res.* 101(1):16-20 (2001); Veeramachaneni, "Down-regulation of Beta Catenin Inhibits the Growth of Esophageal Carcinoma Cells," *J. Thoracic Cardiovasc. Surg.* 127(1):92-98 (2004); U.S. Pat. No. 6,066,500 to Bennett et al., each of which is hereby incorporated by reference in its entirety.

Exemplary siRNA constructs are described in Verma et al., "Small Interfering RNAs Directed Against Beta-catenin Inhibit the in vitro and in vivo Growth of Colon Cancer Cells," *Clin. Cancer Res.* 9(4):1291-300 (2003), which is hereby incorporated by reference in its entirety; and other siRNA against beta-catenin are commercially available from Santa Cruz Biotechnology, Inc.

Exemplary shRNA constructs are described in Gadue et al., "Wnt and TGF-β Signaling are Required for the Induction of an in vitro Model of Primitive Streak Formation using Embryonic Stem Cells," Proc. Natl. Acad. Sci. USA 103(45): 16806-16811, which is hereby incorporated by reference in its entirety; and other shRNA against beta-catenin are commercially available from Super Array Bioscience Corporation, OriGene, and Open Biosystems.

The RNAi agents can be administered directly or administered via gene therapy approach. Thus, DNA molecules (expression vectors) encoding these RNAi agents can also be administered.

For gene therapy approaches, the therapeutic agent, whether a polypeptide or an RNA molecule, can be administered to a patient in the form of a DNA molecule that expresses the therapeutic agent. In vivo, following administration of the DNA molecule, the therapeutic agent is expressed and can exert its effect on the patient for treating a pelvic pain disorder.

Nucleic acid agents (including RNA and DNA) for use in the methods of the present invention can be delivered to a subject in a number of ways known in the art, including through the use of gene therapy vectors and methods as described above. The nucleic acid can be contained within a vector useful for gene therapy, for example, a vector that can be transferred to the cells of a subject and provide for expression of the therapeutic nucleic acid agent therein. Such vectors include chromosomal vectors (e.g., artificial chromosomes), non-chromosomal vectors, and synthetic nucleic acids. Vectors also include plasmids, viruses, and phages, such as retroviral vectors, lentiviral vectors, adenoviral vectors, and adeno-associated vectors.

Nucleic acid agents can be transferred into a subject using ex vivo or in vivo methods. Ex vivo methods involve transfer of the nucleic acid into cells in vitro (e.g., by transfection, infection, or injection) that are then transferred into or administered to the subject. The cells can be, for example, cells derived from the subject (e.g., lymphocytes) or allogeneic cells. For example, the cells can be implanted directly into a specific tissue of the subject or implanted after encapsulation within an artificial polymer matrix. One such site of implantation includes the bladder. Nucleic acids can also be delivered into a subject in vivo. For example, nucleic acids can be administered in an effective carrier, e.g., any formulation or composition capable of effectively delivering the nucleic acid to cells in vivo. Nucleic acids contained within viral vectors can be delivered to cells in vivo by infection or transduction using virus. Nucleic acids and vectors can also be delivered to cells by physical means, e.g., by electroporation, lipids, cationic lipids, liposomes, DNA gun, calcium phosphate precipitation, injection, or delivery of naked nucleic acid.

As an alternative to non-infective delivery of nucleic acids as described above, naked DNA or infective transformation vectors can be used for delivery, whereby the naked DNA or infective transformation vector contains a recombinant gene that encodes, for example, the polypeptide or nucleic acid inhibitor of beta-catenin. The nucleic acid molecule is then expressed in the transformed cell.

The recombinant gene includes, operatively coupled to one another, an upstream promoter operable in mammalian cells and optionally other suitable regulatory elements (i.e., enhancer or inducer elements), a coding sequence that encodes the therapeutic nucleic acid (described above) or polypeptide, and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in the bladder, particularly urothelial cells, such as a uroplakin Ib promoter (Olsburgh et al., "Human Uroplakin lb Gene Structure and Promoter Analysis," Biochim Biophys Acta 1576(1):163-170 (2002), which is hereby incorporated by reference in its entirety) or uroplakin II promoter (Zhang et al., "Identification of Human Uroplakin II Promoter and Its Use in the Construction of CG8840, a Urothelium-specific Adenovirus Variant That Eliminates Established Bladder Tumors in Combination with Docetaxel," Cancer Res 62:3743-3750 (2002), which is hereby incorporated by reference in its entirety); other bladder specific promoters can also be used. Tissue specific promoters can also be made inducible/repressible using, e.g., a TetO response element. Other inducible elements can also be used. Known recombinant techniques can be utilized to prepare the recombinant gene, transfer it into the expression vector (if used), and administer the vector or naked DNA to a patient. Exemplary procedures are described in Sambrook et al., 1-3 MOLECULAR CLONING: A LABORATORY MANUAL (2d ed. 1989), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

It is preferable that the therapeutic agent is administered to the patient in the form of a pharmaceutical composition that includes a pharmaceutically acceptable carrier and one or more active agents that inhibit beta-catenin activity directly by acting on beta-catenin, by promoting beta-catenin degradation, indirectly competing with other agents for binding with beta-catenin, or by interfering with the expression of beta-catenin.

The pharmaceutical compositions of the present invention are preferably in the form of a single unit dosage form that contains an amount of the therapeutic agent that is effective to treat pelvic pain disorders of the type described herein. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

The therapeutic agent, when combined with a suitable carrier and any excipients or stabilizers, and whether administered alone or in the form of a composition, can be administered orally, parenterally, subcutaneously, transdermally, intravenously, intramuscularly, intraperitoneally, by intranasal instillation, by implantation, by intracavitary or intravesical instillation, intraocularly, intraarterially, intralesionally, by application to mucous membranes, such as, that of the nose, throat, and bronchial tubes (i.e., inhalation), or by intrabladder administration. Intravesical administration to the bladder is one suitable route of delivery.

For most therapeutic purposes, the therapeutic can be administered orally as a solid or as a solution or suspension in liquid form, via injection as a solution or suspension in liquid form, or via inhalation of a nebulized solution or suspension.

The solid unit dosage forms containing the therapeutic agent can be of a conventional type. The solid form can be a capsule, such as an ordinary gelatin type containing the therapeutic agent and a carrier, for example, lubricants and inert fillers such as, lactose, sucrose, or cornstarch. In another embodiment, the therapeutic agent is tableted with conventional tablet bases such as lactose, sucrose, or cornstarch in combination with binders like acacia or gelatin, disintegrating agents such as cornstarch, potato starch, or alginic acid, and a lubricant such as stearic acid or magnesium stearate.

For injectable dosages, solutions or suspensions of the therapeutic agent can be prepared in a physiologically and pharmaceutically acceptable diluent as the carrier. Such carriers include sterile liquids, such as water and oils, with or without the addition of a surfactant and other pharmaceutically and physiologically acceptable components, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

For use as aerosols, the therapeutic agent in solution or suspension may be packaged in a pressurized aerosol container together with suitable propellants, for example, hydrocarbon propellants like propane, butane, or isobutane with conventional adjuvants. The therapeutic agent also may be administered in a non-pressurized form such as in a nebulizer or atomizer.

In addition to the above-described formulations which are intended to immediately deliver the therapeutic agents to the patient, sustained release formulations are also contemplated. Preferably, the sustained release formulation is an implantable device that includes a matrix in which the therapeutic agent is captured. Release of the agents can be controlled via selection of materials and the amount of drug loaded into the vehicle. A number of suitable implantable delivery systems are known in the art, such as U.S. Pat. No. 6,464,687 to Ishikawa et al., U.S. Pat. No. 6,074,673 to Guillen, each of which is hereby incorporated by reference in its entirety.

Implantable, sustained release drug delivery systems can be formulated using any suitable biocompatible matrix into which an agent can be loaded for sustained-release delivery. These include, without limitation, microspheres, hydrogels, polymeric reservoirs, cholesterol matrixes, polymeric systems and non-polymeric systems, etc. Exemplary polymeric matrixes include, without limitation, poly(ethylene-co-vinyl acetate), poly-L-lactide, poly-D-lactide, polyglycolide, poly (lactide-co-glycolide), polyanhydride, polyorthoester, polycaprolactone, polyphospagene, proteinaceous polymer, polyether, silicone, and combinations thereof.

Alternatively, for DNA-based therapeutic agents, one suitable vehicle for delivering the therapeutic agent includes solubilized cholesterol as an additive for DNA complexed with a cationic lipid, a cationic polymer, or a dendrimer. Preferably, the cholesterol is solubilized using a cyclodextrin, preferably methyl-β-cyclodextrin. This type of formulation is described in U.S. Patent Publ No. 20020146830 to Esuvaranathan et al., which is hereby incorporated by reference in its entirety.

Use of the inhibitor of beta-catenin in combination with one or more other therapeutic agents is also contemplated. For example, for the treatment of interstitial cystitis, treatment with one of the above-identified inhibitors of beta-catenin in combination with another known treatment of interstitial cystitis including, without limitation, pentosan polysulfate sodium (PPS, Elmiron™), tricyclic antidepressants (amitriptyline, Elavil™), DMSO instillation, oral antihistamines, and combinations thereof.

Thus, the present invention also relates to formulations and therapeutic systems comprising two or more active agents, one of which is the inhibitor of beta-catenin.

By treating pelvic pain, and particularly interstitial cystitis, it is expected that such treatment will be effective in mitigating symptoms associated with the pelvic pain disorder in a patient. This method involves treating the patient for the pelvic pain disorder as described above. Basically, when treating the underlying cause of the pelvic pain disorder, it is believed that management of symptoms can likewise be achieved. By management of symptoms, it is intended that the severity of symptoms can be maintained (i.e., worsening or advancement of symptoms is controlled) or, more preferably, the severity of symptoms can be reduced either in whole or in part.

EXAMPLES

The following examples are provided to illustrate embodiments of the present invention but are by no means intended to limit its scope.

Example 1

Immunohistochemistry on Samples from Interstitial Cystitis Patients

Immunohistochemistry ("IHC") is a powerful technique for visualizing protein expression in the single cell as the sampling unit, but also preserves the social context of the tissue. This strength, and because tissue samples from IC bladders are of limited size and of mixed tissue types, makes IHC a good choice for the proposed studies. Because of the link between antiproliferative factor (APF) and the Wnt receptor frizzled-8 in IC, Wnt signaling was studied in IC patients.

Staining conditions were optimized for an anti-FZD8 antibody (Imgenex, IMX-5081) reactive with the fourth extracellular domain of FZD8. Control tissues also included tissue microarrays containing a variety of human tissues and human pancreas. The peptide recognized by this antibody would be expected to be in the putative APF precursor protein. Examples of FZD8 staining can be seen in FIGS. 1A-B.

Figure 2A:
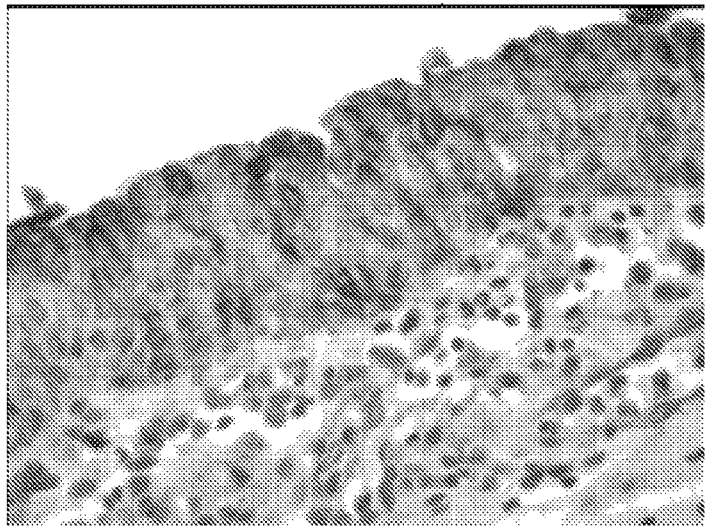
FIGS. 2A-B show immunohistochemistry for beta-catenin in normal urothelium from a bladder cancer patient (FIG. 2A) and in the urothelium of a biopsy from an IC patient (FIG. 2B). Note the distinct membrane distribution of beta-catenin (red staining) and lack of nuclear staining in the normal urothelium. Nuclei are counterstained with hematoxylin (blue). In contrast membrane, cytoplasm, and nuclei are stained positively for beta-catenin in the urothelium of the IC patient.
Figure 2B:
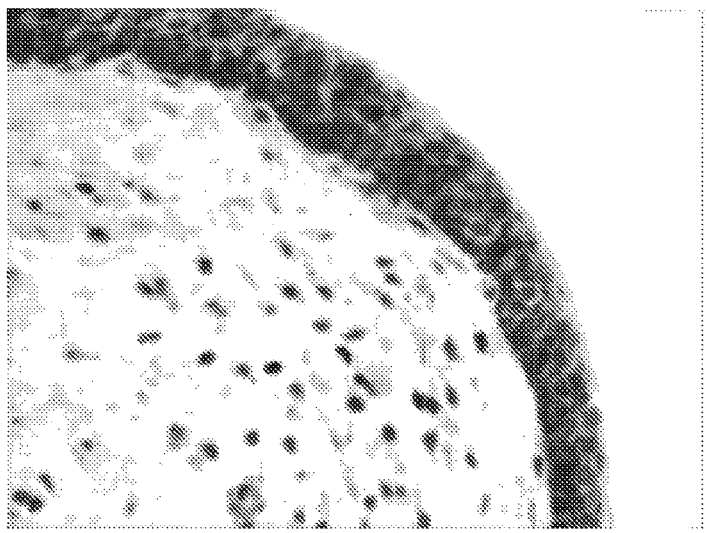

Staining for beta-catenin was carried out with mouse monoclonal antibody (Invitrogen/Zymed catalog #18-0226). Twenty-seven bladder biopsy specimens from IC patients and twelve specimens from patients with bladder cancer were stained for FZD8 and beta-catenin. The bladder cancer specimens were selected for the presence of normal urothelium (as controls) for comparison to the IC specimens. Specimens were classified as positive or negative for FZD8 staining in the urothelium. The beta-catenin staining was evaluated for nuclear staining in the urothelium and separately in the stroma. Positive nuclear staining was defined as greater than 50% of cells with nuclear staining of sufficient intensity to obscure the hematoxylin counter-stain. Examples of negative normal urothelium and stroma from a control specimen, and positive urothelium and stroma in an IC biopsy are presented in FIG. 2A-B. Nuclear beta-catenin staining was not seen in the urothelium of the control specimens.

In this experiment, low levels of beta-catenin staining were observed in bladder cancer. Distinct cell membrane staining was seen in normal urothelium from bladder cancer patients, and most of the bladder cancer cells had a similar pattern. Biopsy specimens from IC patients showed relatively high levels of beta-catenin by immunohistochemistry. These high levels were also associated with distinct nuclear distribution in addition to cell membrane and cytoplasm.

Sixteen of 27 IC biopsies analyzed to date were positive for FZD8 expression, and 18 of 27 specimens had nuclear beta-catenin staining. No nuclear beta-catenin staining was seen in 12 specimens of normal urothelium (or in 32 specimens from a variety of sources contained in a tissue array). Nuclear beta-catenin staining was also observed in colon cancer specimens (as expected) and one bladder cancer specimen. Contingency tables of beta-catenin and FZD8 IHC in the 27 IC biopsy specimens are presented below (Table 1 below).

TABLE 1

Expression of FZD8 and beta-catenin in urothelium of biopsy specimens from IC patients

|  | Nuclear beta-catenin negative | Nuclear beta-catenin positive | Total |
|---|---|---|---|
| FZD8 negative | 5 | 6 | 11 |
| FZD8 positive | 4 | 12 | 16 |
| Total | 9 | 18 | 27 |

By Chi-square and Fisher's Exact Test urothelial and stromal beta-catenin were correlated. FZD8 expression was not correlated with beta-catenin expression.

The level and frequency of nuclear staining in the biopsy specimens indicate a significant and specific alteration in Wnt signaling pathway in IC. Activation of the Wnt pathway triggers translocation of cytoplasmic beta-catenin to the nucleus and these results are therefore quite provocative. It is also quite clear that there is considerable heterogeneity in protein expression and sub-cellular localization among IC patients. Because the natural history of IC follows an unpredictable path, the need for a reliable pathogenomonic marker, like beta-catenin, to aid in diagnosis and selection of therapy could not be greater.

While the above results have been demonstrated in bladder biopsies only, it is expected that exfoliated cells from urine and bladder irrigation specimens of IC patients will also show nuclear beta-catenin staining Either of these samples should prove to be suitable for IC diagnostics.

Example 2

Identification of a Putative APF Precursor Protein

An artificial expression construct for secretion of the APF peptide was constructed. Using the pSecTag2a (Invitrogen) plasmid as a starting point, a fusion gene was built of the immunoglobulin kappa leader sequence (to direct protein for secretion), a furin site for specific cleavage of the protein, and the APF sequence, TVPAAVVVA (SEQ ID NO: 2), followed by a translational stop codon. This plasmid was transfected into a bladder cancer cell line (UM-UC3), the media harvested and analyzed using the antiproliferative activity assay (Keay et al., "a diagnostic in vitro urine assay for interstitial cystitis," *Urology* 52:974-978 (1998), which is hereby incorporated by reference in its entirety). The media from the APF secretion construct had antiproliferative activity (97% inhibition, $p<0.001$) compared to media from cells transfected with just the pSecTag2a plasmid or a plasmid secreting the green fluorescent protein.

To determine how the APF peptide might be produced from the FZD8 protein, the FZD8 amino acid sequence was analyzed (FIG. 3). Examination of the FZD8 amino acid sequence reveals no obvious and specific cleavage sites at either the amino or carboxy side of the APF sequence. However, the fact that APF sits within a transmembrane domain raises another possibility. Like transmembrane domains, signal peptides that target protein sequences for endoplasmic reticulum (ER) and golgi processing are hydrophobic.

The 165 amino acid sequence beginning at position 530 of frizzled-8 was analyzed using SignalP 3.0 (Bendtsen et al., "Improved prediction of signal peptides: SignalP 3.0," *J Mol Biol.* 340(4):783-95 (2004), which is hereby incorporated by reference in its entirety), a program that uses neural network and hidden Markov models to predict signal peptide and cleavage sites in amino acid sequences maintained online by the Technical University of Denmark. The output from this program is shown in FIG. 4. A signal peptide for secretion of this putative APF precursor protein is predicted; and furthermore, appropriate cleavage to produce the known carboxy terminal alanine of APF is predicted. Additional processing would be required for N-terminal glycosylation at the N-terminal threonine of the APF nonapeptide. The ER contains signal peptide peptidases that are known to fragment signal peptides once they have fulfilled the function of targeting proteins to ER-golgi processing.

Significantly, the possibility that the truncated FZD8 protein could insert in the membrane and alter normal FZD8 signaling is an intriguing pathogenic mechanism. Targeted expression of just the intracellular domain of Xenopus frizzled-8 to the plasma membrane was sufficient to trigger apoptosis (Lisovsky et al., "Frizzled receptors activate a novel JNK-dependent pathway that may lead to apoptosis," *Current Biology* 12:53-58 (2002), which is hereby incorporated by reference in its entirety). If this is the case in IC, the lack of pathognomonic hallmarks might be explained by the fact that cells that activate production of APF undergo apoptosis and are lost from the urothelium. The possibility that this putative APF precursor protein might be targeted to the plasma membrane was tested by submitting it for analysis by TMHMM, a computer algorithm for the prediction of transmembrane helices in proteins (Krogh et al., "Predicting transmembrane protein topology with a hidden Markov model: Application to complete genomes," *J. of Molecular Biology* 305:567-580 (2001), which is hereby incorporated by reference in its entirety), also maintained by the Technical University of Denmark. This program predicts the precursor protein would be targeted to the cell membrane and insert with the seventh transmembrane domain in the correct orientation for the carboxy terminal, intracellular domain to interact with intracellular signaling molecules.

While its biological activity may contribute to the production of IC symptoms, APF is obviously downstream of the etiological factors that lead to its production and thus FZD8 abnormalities must be more proximal to those factors. Understanding FZD8 in IC may therefore point to more direct and effective treatment options or diagnostic tests for IC. An abnormal and IC specific FZD8 protein that gives rise to APF could be the result of changes in transcription, translation, or post-translation processing.

To test the capacity of this alternative translational start site to function as a signal peptide, FZD8 coding sequence for amino acids 530 to 694 were amplified from genomic DNA of the full length protein (the APF peptide corresponds to amino acids 541 to 549). This sequence was then fused in frame with the cDNA of enhanced green fluorescent protein (GFP) and the expression plasmid was transfected into the J82 urothelial cell line. Early, transient, and high level expression revealed a morphology consistent with golgi distribution of the green fluorescence. Selection for expression (neomycin resistance) yielded rare colonies with low to moderate levels of expression, perhaps due to APF activity or toxicity of the fusion protein. FIGS. 5A-B are images of a slow growing colony obtained from this transfection. In FIG. 5A, the cytoplasmic, granular fluorescence is consistent with the distribution of a protein in the secretory pathway. FIG. 5B shows the corresponding phase image of the same live cells.

Example 3

FZD8 mRNA Expression by RT-PCR and RACE

Bladder biopsy specimens from IC patients are of limited size and number. The process is complicated by the fact that the RNA preparations must be free of genomic DNA and DNAse treatments can also reduce RNA yields. When a system from Invitrogen using Trizol and on-column digestion of DNA is used, yields ranging from 1.8 to 4 micrograms have been obtained. These yields, while adequate for procedures employing amplification strategies, are not adequate for the more traditional blotting methods. Thus, interrogation of the FZD8 gene expression required use of RT-PCR and Rapid Amplification of cDNA Ends ("RACE").

Because FZD8 is an intronless gene, genomic DNA as PCR template is acceptable to construct the expression plasmid. First, a PCR product that had the desired 5' and 3' ends in frame but lacked the sequence encoding the glycine rich region in the intracellular carboxy end of the putative precursor protein was obtained (FIG. 3). The stretch of glycine residues is encoded by a nucleotide sequence of 102 nucleotides of which only three are not G or C. At the time of this observation, first attempts at reverse transcription of the FZD8 mRNA were made. This unusually long GC rich region might complicate the reverse transcription (RT) from poly-T primers as well as the subsequent PCR steps. Using random primers for the RT reaction and including 5% dimethyl sulfoxide in the PCR reaction was successful. A control reaction omitting the reverse transcriptase from the reaction mix was included in all procedures to rule out the possibility that any product was produced from contaminating genomic DNA.

A transcript with the capacity to encode the putative APF precursor protein was tested for using random primers for the RT reaction, a PCR sense-strand primer (ATGATCCGC-CTGGGCCTGTTCACCGTGCTC, SEQ ID NO: 6) corresponding to the putative translational start and an anti-sense primer just 5' to the GC-rich region (CTGGCCCAGCAG-CAGCGGGTGCACA, SEQ ID NO:7). The expected 284 basepair product was obtained from eight bladder biopsy specimens, seven from IC patients and one from a non-IC control subject. The cDNA was also successfully amplified from RNA isolated from three of three bladder irrigation specimens from IC patients.

Total RNA was isolated from J82 cells, one of the cell lines that expresses a small FZD8 protein isoform. RNA ligase mediated RACE (RLM-RACE) is a very specific and sensitive RACE procedure, and using this technique the 5' end of a FZD8 transcript in J82 cells was defined that could give rise to the putative APF precursor protein. The sequence of this RLM-RACE product is shown in FIG. 6. Several attempts to obtain RACE products using anti-sense primers in the PCR reaction that are closer to the start of the full length FZD8 open reading frame but no longer sequences have been obtained. These data support the belief that aberrant FZD8 transcripts can be translated and cleaved to produce small FZD8 isoforms such as APF.

Example 4

Analysis of IC Biopsy Specimens by RNA Ligase-mediated Rapid Amplification of cDNA Ends (RLM-RACE)

RLM-RACE was performed on two IC biopsy specimens (BM19 and BM21), two bladder cancer cell lines (J82 and T24), and normal pancreas (PanN) and pancreatic cancer (PanT) (positive controls). RLM-RACE products were cloned and sequenced substantially as described above.

RLM-RACE products were aligned (FIG. 7) with human genomic DNA using the UCSC Genome Browser available online. FZD8 is an intronless gene, with the protein coding sequence oriented from right to left in FIG. 7. The position of the APF peptide in the FZD8 coding sequence is shown in the figure as well. RLM-RACE products with the capacity to code for the putative APF precursor protein were obtained from J82 and T24 cell lines. This transcript was not detected in IC biopsies or the pancreas specimens. These specimens did, however, yield RLM-RACE products more proximal to the 5' end of the FZD8 open reading frame, as did one of the cell lines (T24). Both the large and small proteins isoforms are expressed in T24 cells.

In summary, evidence exists from this study for a putative APF precursor transcript in two cell lines but no evidence for the abbreviated transcript in IC biopsies, or pancreas although these specimens did yield RLM-RACE FZD8 products. The small FZD8 protein isoform has been found in J82 and T24 cells on western blots. A FZD8 isoform greater than 70 kilodaltons has been found in pancreas, pancreatic tumor, IC biopsies, and T24 cells.

The data in this example lends further support to the finding of Wnt pathway activation in IC. The small FZD8 protein isoform and the alternative transcriptional start site detected by RLM-RACE support the belief that APF production is caused by the aberrant FZD8 transcription and post-translational cleavage to produce small FZD8 isoforms.

Example 5

FZD8 Protein Expression

FZD8 protein was detected in analysis of anonymous control urines for method development. These results are very encouraging for a direct mass spectrometry (MS) confirmation of APF in urine well as the possibility of characterizing FZD8 isoforms in urine and tissue.

Urine samples were dialyzed against water and digested using trypsin prior to lyophilization. Lyophilized samples were dissolved in 50 mL of 2% acetonitrile/98% water/0.1% formic acid. This solution was diluted to 20 mL with 0.1% formic acid and injected into LC. Separation was conducted Ultimate 3000 LC system (Dionex) using a Dionex C18 PepMap100 column (180 mm I.D.×15 cm) at a rate of 1.5 mL/min. Total duration of the LC run was 150 min with 128 min gradient. Automated spotting performed on Proteineer FC robot (Bruker Daltonics) using Prespotted Anchor Chip (PAC) target. The LC-MALDI run consisted of 384 spots deposited in 20 s intervals with collected from 4 min to 132 min of each run. MALDI-TOF/TOF analyses were carried out on an Autoflex III TOF/TOF mass spectrometer (Bruker Daltonics) equipped with 200 Hz smartbeam laser. The automated LC-MALDI run was set up in WARP-software (Bruker Daltonics) and included automated acquisition and processing of MALDI-TOF and MALDI-TOF/TOF spectra followed by Mascot MS/MS database search using combined peak list from all acquired and MS/MS spectra and visualization of search results in spreadsheet and graphical formats.

Among greater than 200 proteins uniquely identified, three unique peptides of FZD8 were found. These were: YGFAW-PDR (SEQ ID NO: 8), YETTGPALCT (SEQ ID NO: 9), and GAGAAGAGAGGPGGR (SEQ ID NO: 10). This was not an IC patient, but an anonymous control who may or may not have disease of the GU system or other unspecified disease. The data demonstrate that FZD8 protein can be present and detectable by MS in urine.

The Imgenex antibody, IMX-3907, is reactive with a peptide sequence at the carboxy terminus of FZD8. The sequence is conserved between mouse, rat, and human. The peptide overlaps the FZD8 sequence which interacts with the GOPC protein (Yao et al., "Identification of a PDZ domain containing golgi protein, GOPC, as an interaction partner of frizzled," *Biochemical and Biophysical Research Communications* 286:771-778 (2001), which is hereby incorporated by reference in its entirety). Expression of FZD8 was assayed in several mouse tissues to validate the antibody. In addition to tissues from wildtype (FVB/N) mice protein from UPII-SV40T mice was also sampled. These transgenic mice, supplied by Dr. T. T. Sun of New York University, express the simian virus 40 large T antigen protein under the control of the uroplakin II promoter (Johnson et al., "Early Detection and Measurement of Urothelial Tumors in Mice," *Urology* 67:1309-1314 (2006), which is hereby incorporated by reference in its entirety). They reliably develop bladder tumors. Organs were harvested, following euthanasia ($CO_2$ inhalation). The tissues were immediately frozen in liquid nitrogen. Tissues were homogenized in lysis buffer with a protease inhibitor cocktail. Protein concentrations were determined by Bradford assay and 35 micrograms of protein loaded on minigels, in the presence of 1% beta-mercaptoethanol. The western blot with IMX-3907 and chemiluminescence detection produced some surprising results.

Figure 8:
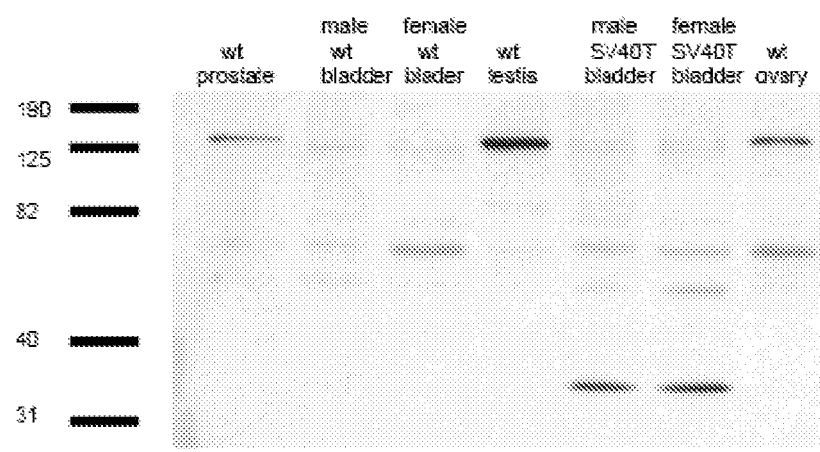
FIG. 8 shows FZD8 protein expression in mouse tissues. Molecular weight standards are shown on the left in kilodaltons. The western blot was probed with the IMX-3907 antibody, reactive with the carboxy terminal of FZD8. The full length (694 amino acid) un-modified FZD8 protein has an anticipated molecular weight of 73 kilodaltons. A band of this approximate molecular weight can be seen to a greater or lesser extent in all lanes. The strong band above 125 kilodaltons may be a hetero- or homodimer. Both tumor-bearing bladder specimens have a relatively small protein between 31 and 40 kilodaltons.

The result of the tissue survey is shown in FIG. 8. First, note that there is a protein band at the anticipated full length FZD8 molecular weight of 73 kilodaltons in most tissues. There is also a tissue specific band between 125 and 190 kilodaltons. At the present time, this is believed to represent either a homo- or heterodimer. A stable homodimer like this has been shown on western blots for frizzled-3 (Carron et al., "Frizzled receptor dimerizatino is sufficient to activate the Wnt/beta-catenin pathway," *J Cell Science* 116:2541-2550 (2003), which is hereby incorporated by reference in its entirety), and dimerization was sufficient to activate the Wnt/beta-catenin pathway. Also, note that the bladders from both UPII-SV40T mice contain a much smaller isoform between 31 and 40 kilodaltons in size. The data indicate several tissue specific (and cancer specific) FZD8 protein expression patterns. The putative dimer was seen in pancreas, seminal vesicle, prostate, testis, ovary, and liver. Skin and bladder contain relatively little or none of the dimer. There is a minor band at the higher molecular weight in bladder, but as can be seen in FIG. 8, it appears at a slightly lower position on the blot than the strong signal seen in prostate and testis. Kidney was negative for protein, despite the fact that FZD8 staining was observed by immunohistochemistry in human kidney. Other mouse tissues that were negative included spleen, brain, intestine, skeletal muscle, heart, and lung.

Figure 9:
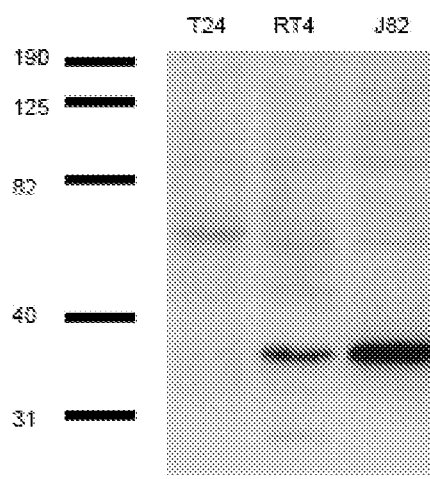
FIG. 9 shows FZD8 protein expression in tissue culture cell lines. The western blot was probed with IMX-3907 antibody. A band corresponding to full length FZD8 protein (73 kilodaltons) can be seen in the T24 cells. Both RT4 and J82 cells have a band between 31 and 40 kilodaltons similar to that observed in mouse bladder cancer.

FZD8 expression in cell lines were also examined. Cells were lysed in the presence of protease inhibitors. A full length FZD8 protein was observed in T24 cells on the western blot (FIG. 9). RT4 and J82 cells, however, show a band corresponding in size to that observed in the mouse bladder cancer samples, between 31 and 40 kilodaltons.

These data indicate that FZD8 has tissue and disease specific expression and isoforms, and that protein-protein interactions are tissue and disease specific. The larger than expected sizes may depend upon expression of other proteins that are present in stable multi-protein complexes with FZD8 or ligands that trigger the dimerization. The smaller than expected sizes could be the result of alternative transcripts, alternative translations, or post-translational modifications of the type described above.

Figure 10:
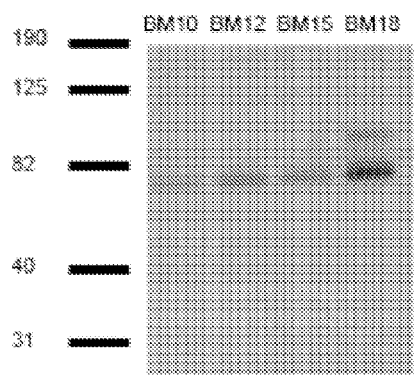
FIG. 10 shows FZD8 protein expression in bladder biopsy specimens. The western blot was probed with IMX 3907 antibody. A band corresponding to full length FZD8 is seen in all specimens. In one specimen there is a higher molecular weight band.

A limited number of IC biopsy specimens were analyzed for FZD8 expression by western blot. The specimens, obtained during cystoscopy are small in size and no attempt has been made to determine the relative mix of urothelium to sub-mucosal structures. It may be possible to use a urothelial marker, such as a uroplakin, to normalize protein yield from urothelium. Four biopsy specimens were snap frozen in liquid nitrogen at time of collection. The specimens were homogenized in lysis buffer in the presence of protease inhibitors. Western blot with antibody IMX-3907 revealed a major band in all four IC specimens (FIG. 10). In addition there was a shift to a larger molecular weight in one specimen (BM18), which may reveal a protein-protein interaction.

Example 6

Mass Spectrometry Analysis of Urine Proteins

Urine (25 ml) was prepared using published methodology (Conrads et al. "CKAP4/p63 is a Receptor for the Frizzled-8 Protein-related Antiproliferative Factor from Interstitial Cystitis Patients," *J. Biol. Chem.* 281:37836-37843 (2006), which is hereby incorporated by reference in its entirety) or using variations of solid-phase extraction (Dettmer et al., "Autism and Exogenous Neuropeptides: Development of an On-line SPE-HPLC-tandem Mass Spectrometry Methods to Test the Opiodi Excess Theory," *Anal Bioanal Chem.* 388:1643-1651 (2007), which is hereby incorporated by reference in its entirety) to determine the presence of APF. Urine proteins were applied to a micro-capillary liquid chromatography system coupled to the LTQ-MS instrument using an in-line analytical capillary column packed using C18 reversed-phase resin and capillary tubing pulled to <5 mm open point. Samples were loaded on their own individual columns using a home built pressure bomb. Peptides were eluted using a linear gradient of 5-70% solvent (to a final working concentration of 0.1% acetic acid in solution of 95% acetonitrile and 5% water over 45 min). Each sample was run in a survey mode and SRM mode with molecular weights of APF and predicted fragments of 1482.8, 1191.5, 1029.5, 826.5 as well as their 2+ and 3+ charge states. Although several biologically active urine peptides are detectable by these methods (including but not limited to epidermal growth factor), the APF peptide was not present to the limit of detection (5 femptomole) as determined using synthetic APF peptide.

Figures 11A, 11B, 11C:
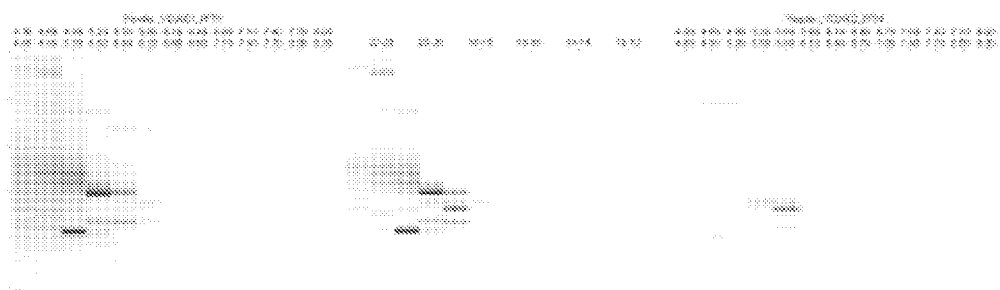
FIG. 11A-C show PF2D analysis of control and IC urine proteins.

Urine specimens from IC patients and control subjects were separated using a Beckman Coulter ProteomeLab PF2D protein fractionation system with minor modifications to a method previously described (Khurana et al., "Urine Proteomic Profiling of Pediatric Nephrotic Syndrome," *Pediatr Nephrol.* 21(9):1257-1265 (2006), which is hereby incorporated by reference in its entirety). The data are displayed as virtual 2D arrays and differentially expressed proteins identified by comparison of two or more specimens. The PF2D liquid/liquid system is particularly efficient in detection and identification of membrane bound materials (Smith, "Proteomics: Challenges and Emerging Technologies," *EuroSciCon. Expert Rev. Proteomics* 3:573-577 (2006), which is hereby incorporated by reference in its entirety). Five mg of extracted proteins and peptides from either controls or IC patients were injected for automated runs. FIGS. 11A-C illustrate the output from two compared runs using DeltaView software (Beckman Coulter). In FIG. 11A the 2-dimensional array has the isoelectric function across the top with the hydrophobicity separation going from low (top) to high (bottom). The 2-dimensional array shown in FIG. 11C is from a patient sample (with IC) and FIG. 11B shows a composite resultant array showing the difference in their output. Many of the differing materials have been identified. Identification of specific proteins is possible by selecting specific aliquots from the separation and subsequent MALDI-TOF analysis. These data, in combination with additional data to be generated, will afford a database for urine and tissue proteomics that will be useful for assessing Wnt pathway protein expression.

Example 7

Construction of Full-length FZD8 Reporter Plasmid with Native Promoter

A plasmid was constructed and verified containing the 2082 basepair FZD8 open reading frame and 1500 basepairs upstream from the putative translational start site. (For open reading frame and upstream regions of FZD8, see Genbank Accessions NM_031866 and AL121749, respectively, each of which is hereby incorporated by reference in its entirety.) The stop codon was mutated to glycine to enable read-through to reporter proteins (GFP and luciferase).

The putative promoter and open reading frame will be inserted into pZsGreen1-DR (Clontech, GFP reporter) and pGL3 (Promega, luciferase reporter) plasmids. Following ligation into the plasmids and bacterial transformation, selected plasmid clones will be fully sequenced. Immortalized urothelial cells and urothelial cell lines T24 and J82 will be used to characterize the FZD8 promoter. Cells expressing GFP can be observed live following transfection. Because the ZsGreen1-DR protein is a destabilized variant of GFP, this reporter protein has a short half-life of only a few hours. As such its abundance reflects promoter activity in the short-term. This permits an assessment of the proportion of cells with an active promoter. The luciferase reporter is a reliable way to quantify total gene expression within a population.

Green fluorescence, western blotting and luciferase assays will be used to identify essential promoter elements. RACE will be performed to determine the 5' end of transcripts in various cell types and under various culture conditions. Western blotting with antibodies for FZD8, GFP, and luciferase activity will be used to characterize fusion proteins.

Transfected cells containing the GFP and luciferase reporter plasmids will also be used to determine the activity of the promoter relative to proliferation (cell cycle affects), hormonal stimuli (estradiol, testosterone, dihydrotestosterone), and stress (heat, hypoxia). The cells will be incubated in defined media and the response of the promoter to the stimulus across time and concentrations evaluated. Cells will be examined live using inverted fluorescence microscopy. They will be harvested and counter-stained for DNA content (cell cycle analysis) relative to green fluorescence and FZD8 promoter activity. The response of the promoter to stress will be evaluated by subjecting the cells to temperatures above or below standard 37° C. incubation temperatures. Live cells will be monitored over time at temperatures ranging from 34° C. to 42° C. Phase contrast images and green fluorescence images will be recorded using techniques previously described (Wright et al., "DBCCR1 mediates death in cultured bladder tumor cells," *Oncogene* 23:82-90 (2004), which is hereby incorporated by reference in its entirety). Similarly, the response of the promoter to hypoxic conditions using defined atmospheric conditions in non-bicarbonate, HEPES buffered media will be tested. Again, live cells will be monitored and imaged over time to determine if green fluorescence is increased or decreased in response. Positive results will be followed by western blot of proteins associated with stress responses beginning with heat shock proteins.

Example 8

Assessment of Wnt Signaling by DNA Array

Based on the finding of nuclear beta-catenin in IC biopsies (Example 1), other Wnt signal pathway genes will be assessed in response to hormonal stimuli because of the large difference between the sexes in the incidence of IC. Real-time PCR arrays will be used in triplicate. These arrays contain 84 genes associated with Wnt signaling. Mean expression levels will be compared using t-tests with Bonferroni correction and changes in gene expression will be verified by additional real-time PCR and western blotting.

Example 9

Treatment of Interstitial Cystitis

Female patients diagnosed with interstitial cystitis and demonstrated by biopsy to have elevated beta-catenin expression will be administered a DNA molecule that expresses an RNAi therapeutic agent (that silences beta-catenin) in a formulation containing solubilized cholesterol as an additive to DNA complexed with a cationic lipid, a cationic polymer or a dendrimer (see U.S. Patent Publ. No. 20020146830 to Esuvaranathan et al., which is hereby incorporated by reference in its entirety). The formulation will be administered directly into the bladder in varying amounts (10 to 500 μg) to assess effective dosage levels. Control patients will receive vehicle only.

Efficacy of the treatment will be assessed by monitoring symptoms of IC as well as biopsy results to assess beta-catenin levels in urothelial cells of treated patients.

Example 10

Treatment of Interstitial Cystitis

Female patients diagnosed with interstitial cystitis and demonstrated by biopsy to have elevated beta-catenin expression will be administered one of PKF115-584, PKF-222-815, or CPG049090 either intravenously or via intra-bladder administration in dosages varying from 10 mg to 100 mg daily. Control patients will receive vehicle only. Efficacy of the treatment will be assessed by monitoring symptoms of IC as well as biopsy results to assess beta-catenin levels in urothelial cells of treated patients.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A method for diagnosing interstitial cystitis comprising: (a) obtaining a sample comprising urothelium cells from a subject suspected of having interstitial cystitis; and (b) analyzing said sample or a fraction thereof for increased nuclear localization of beta-catenin;

and (c) comparing the nuclear localization of beta-catenin in the sample or fraction from the subject suspected of having interstitial cystitis with the nuclear localization of beta-catenin in a control sample or fraction thereof, wherein increased nuclear localization of beta-catenin, as compared to the control, supports a diagnosis of interstitial cystitis.

2. The method according to claim 1 wherein said analyzing comprises measuring beta-catenin protein levels.

3. The method according to claim 2 wherein said measuring beta-catenin protein levels is carried out with an antibody specific for beta-catenin or a binding portion thereof.

4. The method according to claim 1 wherein said control sample or fraction thereof is obtained from a normal subject.

5. The method according to claim 1, wherein said sample comprises a fine needle aspiration, a core needle biopsy, a surgical biopsy, a vacuum-assisted biopsy, a biopsy using an advanced breast biopsy instrument, a surgical specimen, a paraffin embedded tissue or a frozen tissue imprint.

6. The method according to claim 1, wherein a nuclear fraction from the samples is analyzed.

7. The method according to claim 6, further comprising isolating a nuclear fraction from the samples prior to said analyzing.

* * * * *